(12) United States Patent
Bektesevic et al.

(10) Patent No.: US 10,343,962 B2
(45) Date of Patent: *Jul. 9, 2019

(54) PROCESS FOR PRODUCING 2,3,3,3-TETRAFLUOROPROPENE

(71) Applicant: HONEYWELL INTERNATIONAL INC., Morristown, NJ (US)

(72) Inventors: Selma Bektesevic, Williamsville, NY (US); Daniel C. Merkel, West Seneca, NY (US); Mario Joseph Nappa, Newark, DE (US); Xuehui Sun, Swedesboro, NJ (US); Hsueh Sung Tung, Getzville, NY (US); Haiyou Wang, Amherst, NY (US)

(73) Assignee: Honeywell International Inc., Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/464,439

(22) Filed: Mar. 21, 2017

(65) Prior Publication Data

US 2017/0253544 A1 Sep. 7, 2017

Related U.S. Application Data

(60) Division of application No. 14/355,974, filed as application No. PCT/US2012/063320 on Nov. 2, (Continued)

(51) Int. Cl.
*C07C 17/42* (2006.01)
*C07C 17/20* (2006.01)
(Continued)

(52) U.S. Cl.
CPC ............ *C07C 17/42* (2013.01); *C07C 17/087* (2013.01); *C07C 17/206* (2013.01); *C07C 17/25* (2013.01); *C07C 19/10* (2013.01); *C07C 21/18* (2013.01)

(58) Field of Classification Search
None
See application file for complete search history.

(56) References Cited

U.S. PATENT DOCUMENTS 2,931,840 A 4/1960 Marquis et al.
4,900,874 A 2/1990 Ihara et al.
(Continued)

FOREIGN PATENT DOCUMENTS

CN 101597209 A 12/2009
CN 101665403 A 3/2010
(Continued)

OTHER PUBLICATIONS

Notification of Reasons for Rejection issued in Japanese Application No. 2014-540134 dated Jul. 12, 2016 (in English and Japanese).
(Continued)

*Primary Examiner* — Clinton A Brooks
(74) *Attorney, Agent, or Firm* — Faegre Baker Daniels LLP

(57) ABSTRACT

The present invention relates, in part, to the discovery that, during the fluorination of certain fluoroolefin starting reagents, particularly, 1,1,2,3-tetrachloropropene (1230xa), oligomerization/polymerization of such starting reagents reduces the conversion process and leads to increased catalyst deactivation. The present invention also illustrates that providing one or more organic co-feed to the fluooolefin starting stream reduces such oligomerization/polymerization and improves catalystic stability.

26 Claims, 1 Drawing Sheet

Related U.S. Application Data 2012, now Pat. No. 9,670,117, which is a continuation-in-part of application No. 13/302,849, filed on Nov. 22, 2011, now Pat. No. 8,754,271, which is a division of application No. 11/619,592, filed on Jan. 3, 2007, now Pat. No. 8,084,653.

(60) Provisional application No. 61/555,682, filed on Nov. 4, 2011.

(51) Int. Cl.
| | |
|---|---|
| *C07C 17/25* | (2006.01) |
| *C07C 17/087* | (2006.01) |
| *C07C 19/10* | (2006.01) |
| *C07C 21/18* | (2006.01) |

(56) References Cited

U.S. PATENT DOCUMENTS

| | | | |
|---|---|---|---|
| 5,155,082 | A | 10/1992 | Tung et al. |
| 5,162,594 | A | 11/1992 | Krespan |
| 8,058,486 | B2* | 11/2011 | Merkel .................. C01B 7/035 |
| | | | 570/135 |
| 8,067,649 | B2* | 11/2011 | Kopkalli ............... C07C 17/087 |
| | | | 570/135 |
| 8,084,653 | B2 | 12/2011 | Tung et al. |
| 8,754,271 | B2* | 6/2014 | Mukhopadhyay ...... C07C 17/00 |
| | | | 570/123 |
| 9,328,043 | B2* | 5/2016 | Wang .................. C07C 17/206 |
| 9,399,609 | B2* | 7/2016 | Wang .................. C07C 17/23 |
| 2007/0197842 | A1 | 8/2007 | Mukhopadhyay et al. |
| 2009/0030244 | A1* | 1/2009 | Merkel ................. C07C 17/206 |
| | | | 570/135 |
| 2009/0030247 | A1 | 1/2009 | Johnson et al. |
| 2009/0240090 | A1 | 9/2009 | Merkel et al. |
| 2010/0036179 | A1 | 2/2010 | Merkel et al. |
| 2010/0072415 | A1* | 3/2010 | Rao ........................ B01J 23/26 |
| | | | 252/67 |
| 2011/0105807 | A1 | 5/2011 | Kopkalli et al. |
| 2011/0130599 | A1 | 6/2011 | Elsheikh et al. |
| 2011/0155942 | A1 | 6/2011 | Pigamo et al. |
| 2014/0256996 | A1* | 9/2014 | Wang .................... C07C 17/087 |
| | | | 570/160 |
| 2015/0152028 | A1 | 6/2015 | Johnson et al. |

FOREIGN PATENT DOCUMENTS

| | | |
|---|---|---|
| CN | 101874009 A | 10/2010 |
| JP | 2009-227675 A | 10/2009 |
| JP | 2010-534680 A | 11/2010 |
| JP | 2014-532721 A | 12/2014 |
| KR | 10-2010-0039352 A | 4/2010 |
| WO | 2009/015317 A1 | 1/2009 |
| WO | WO2010123148 A1 | 10/2010 |
| WO | 2011/056441 A2 | 5/2011 |
| WO | WO 2011/087825 A1 | 7/2011 |
| WO | WO2011110889 A1 | 8/2011 |
| WO | 2013/067356 A1 | 5/2013 |

OTHER PUBLICATIONS

Banks, R.E. et al., Preparation of 2,3,3,3-tetrafluoropropene from trifluoroacetylacetone and sulphur tetrafluoride, Journal of Fluorine Chemistry, (1997), vol. 82, pp. 171-174.
International Search Report dated Mar. 8, 2013 issued in PCT/US2012/063320.
Supplementary European Search Report dated May 6, 2015 corresponding to European Patent Appln. No. EP 12 84 5281.
Chinese Office Action dated Mar. 31, 2015 corresponding to Chinese Patent Appln. No. 201280065884.8.
First Office Action and Search Report issued in corresponding Chinese Patent Application No. 201810741773.4 dated Jun. 5, 2018.
Examination report under sections 12 & 13 of the Patents Act, 1970 and the Patents Rules, 2003., issued in corresponding Indian Application No. 3382/DELNP/2014 dated Apr. 24, 2018.
Notice of Reasons for Rejection dated May 2, 2018 issued in corresponding Japanese Patent Application No. 2017-141782.
Office Action dated Dec. 13, 2018, issued in corresponding Korean Patent Application No. 10-2014-7011881.

* cited by examiner

PROCESS FOR PRODUCING 2,3,3,3-TETRAFLUOROPROPENE

CROSS REFERENCE TO RELATED APPLICATIONS

This application is a divisional of U.S. patent application Ser. No. 14/355,974, filed May 2, 2014, which is a '371 of PCT Application No. PCT/US2012/063320, filed on Nov. 2, 2012, which claims priority to U.S. Provisional Application No. 61/555,682 filed on Nov. 4, 2011. U.S. patent application Ser. No. 14/355,974, filed May 2, 2014 is also a continuation-in-part of U.S. patent application Ser. No. 13/302,849, filed on Nov. 22, 2011, now U.S. Pat. No. 8,754,271, filed Jun. 17, 2014, which is a divisional of U.S. patent application Ser. No. 11/619,592, filed Jan. 3, 2007, now U.S. Pat. No. 8,084,653, issued on Dec. 27, 2011, the contents each of all of the foregoing are incorporated herein by reference.

FIELD OF THE INVENTION

The present invention relates to a process for preparing fluorinated organic compounds, more particularly to a process for preparing fluorinated olefins, and even more particularly to a process for producing 2,3,3,3-tetrafluoropropene (HFO-1234yf).

BACKGROUND OF THE INVENTION

Hydrofluoroolefins (HFOs), such as tetrafluoropropenes (including 2,3,3,3-tetrafluoropropene (HFO-1234yf), are now known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

Several methods of preparing HFOs are known. For example, U.S. Pat. No. 4,900,874 (Ihara et al) describes a method of making fluorine containing olefins by contacting hydrogen gas with fluorinated alcohols. Although this appears to be a relatively high-yield process, commercial scale handling of hydrogen gas at high temperature is hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

However, there remains a need for an economic means of producing hydrofluoroolefins, such as HFO-1234yf. The present invention satisfies this need among others.

SUMMARY OF INVENTION

The present invention relates, in part, to one or more process steps for improving the reaction efficiency used for the production of HFOs, such as 2,3,3,3-tetratluoropropene (1234yf).

In one aspect, the present invention relates to a process for preparing 2-chloro-3,3,3-trifluoropropene by providing a starting composition including at least one compound of formula I

$$CX_2=CCl-CH_2X \qquad (I)$$

wherein X is independently selected from F, Cl, Br, and I, provided that at least one X is not fluorine and contacting said starting composition with a fluorinating agent and an effective amount of one or more organic co-feed compounds, other than the compound of formula I, to produce a final composition comprising 2-chloro-3,3,3-trifluoropropene. In certain embodiments, at least one compound of formula I has at least one X is a chlorine. In further embodiments, at least one compound of formula I has a chlorine at each X position. In even further embodiments, at least one compound of formula I includes 1,1,2,3-tetrachloropropene.

The organic co-feed compound may be any organic compound that improves the foregoing process, particularly by decreasing starting reagent oligomerization/polymerization and/or reducing catalyst deactivation over the course of the process. In one embodiment, the organic co-feed compound has a boiling point that is lower than the compound of Formula I. Such compounds include halocarbons or haloolefins, of which one or more of the following may be included: trichlorofluoropropene (1231), dichlorodifluoropropene (1232), 1,2-dichloro-3,3,3-trifluoropropene (1223xd), 2-chloro-3,3,3-trifluoropropene (1233xf), 2,3,3,3-tetrafluoroprop-1ene (1234yf), 2-chloro-1,1,1,2-tetrafluoropropane (244bb), and 1,1,1,2,2-pentafluoropropane (HFC-245cb), 1,1,1,2,3-pentafluoropropane (245eb), tetrachlorofluoropropane (241), trichlorodifluoropropane (242), dichlorotrifluoropropane (243).

The effective amount of the co-feed compound may be any amount provided herein. While not limited thereto, in certain aspects, it is between about 0.1 to about 99.9 wt %, between about 1 to about 50 wt %, between about 3 to about 30 wt %, or between about 5 to about 15 wt %, each based on the total amount of organic feed provided to the reaction.

The step of contacting the starting composition with a fluorinating agent may occur in the presence of a catalyst. In one aspect, the contacting step occurs in a vapor phase with or without the presence of a vapor phase catalyst. Vapor phase catalysts used for such a reaction include, but are not limited to, a chromium oxide, a chromic hydroxide, a chromium halide, a chromium oxyhalide, an aluminum oxide, an aluminum hydroxide, an aluminum halide, an aluminum oxyhalide, a cobalt oxide, a cobalt hydroxide, a cobalt halide, a cobalt oxyhalide, a manganese oxide, a manganese hydroxide, a manganese halide, a manganese oxyhalide, a nickel oxide, a nickel hydroxide, a nickel halide, a nickel oxyhalide, an iron oxide, an iron hydroxide, an iron halide, an iron oxyhalide, inorganic salts thereof, fluorinated derivatives thereof and combinations thereof. In certain embodiments, the catalyst includes a chromium oxide, such as, but not limited to, $Cr_2O_3$.

The step of contacting the starting composition with a fluorinating agent also may occur in the presence of one or more stabilizers. Such stabilizers may include amine-based stabilizer, of which one or more of the following may be included: p-tap(4-tert-Amylphenol), methoxy-hydroquinone, 4-methoxyphenol(HQMME), triethylamine, di-isopropyl amine, butylated hydroxy anisole (BHA), and thymol.

In even further aspects, the present invention relates to a process for preparing 2,3,3,3-tetrafluoroprop-1-ene by
a. providing a starting composition including a compound of formula I

$$CX_2\!=\!CCl\!-\!CH_2X \qquad (I)$$

wherein X is independently selected from F, Cl, Br, and I, provided that at least one X is not fluorine;
b. contacting the starting composition with a first fluorinating agent and an effective amount of one or more organic co-feed compounds, other than the compound of formula I, to produce a first intermediate composition including 2-chloro-3,3,3-trifluoropropene and a first chlorine-containing byproduct;
c. contacting the first intermediate composition with a second fluorinating agent to produce a second intermediate composition including 2-chloro-1,1,1,2-tetrafluoropropane; and
d. dehydrochlorinating at least a portion of the 2-chloro-1,1,1,2-tetrafluoropropane to produce a reaction product including 2,3,3,3-tetrafluoroprop-1-ene.

Additional embodiments and advantages to the present invention will be readily apparent to one of skill in the art, based on the disclosure provided herein.

DETAILED DESCRIPTION OF THE INVENTION

Figure 1:
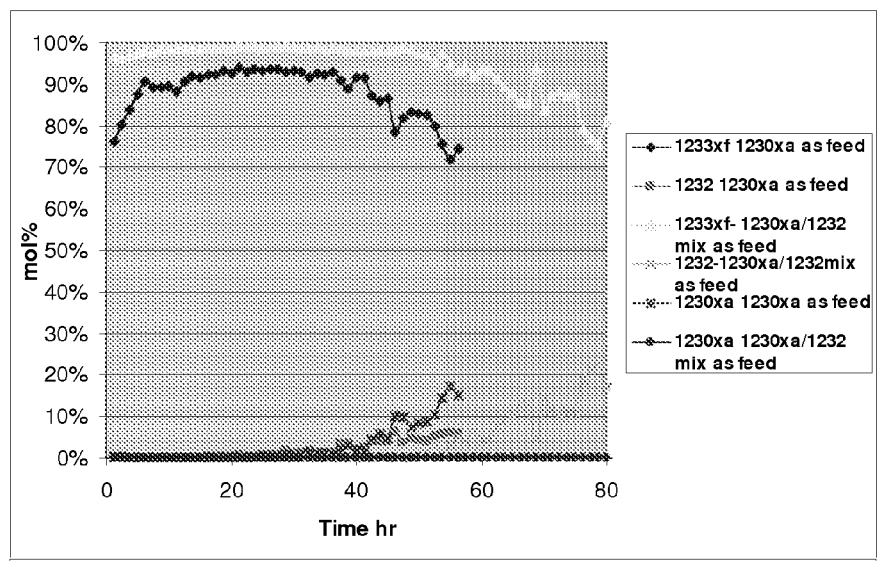
FIG. 1 provides a comparative illustration of catalytic deactivation during fluorination of 1230xa to form 1233xf in the absence or presence of a 1232xf co-feed.

According to one embodiment, the present invention includes a manufacturing process for making 2,3,3,3-tetrafluoroprop-1-ene using a starting material according to formula I:

$$CX_2\!=\!CCl\!-\!CH_2X \qquad \text{(Formula I)}$$

wherein X is independently selected from F, Cl, Br, and I, provided that at least one X is not fluorine. In certain embodiments, the compound(s) of Formula I contains at least one chlorine, a majority of the Xs as chlorine, or all Xs as chlorine. In certain embodiments, the compound(s) of formula I include 1,1,2,3-tetrachloropropene (1230xa). Processes applicable to the present invention include, without limitation, integrated multistep processes as described in U.S. Pat. No. 8,084,653 and US Published Patent Application 2009/0240090, the contents of each of which are incorporated herein by reference.

The method generally includes at least three reaction steps. In the first step, a starting composition of Formula I (such as 1,1,2,3-tetrachloropropene) is reacted with anhydrous HF in a first vapor phase reactor (fluorination reactor) to produce a mixture of 2-chloro-3,3,3-trifluoropropene (1233xf) and HCl. In certain embodiments, the reaction occurs in the vapor phase in the presence of a vapor phase catalyst, such as, but not limited to, a fluorinated chromium oxide. The catalyst may (or may not) have to be activated with anhydrous hydrogen fluoride HF (hydrogen fluoride gas) before use depending on the state of the catalyst. In one embodiment, there is no oxygen-containing agent or gas feed, e.g. air, pure oxygen, or diluted oxygen gas, such as an oxygen/inert gas (e.g. nitrogen), to the first vapor phase reactor.

While fluorinated chromium oxides are disclosed as the vapor phase catalyst, the present invention is not limited to this embodiment. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures and any one of which may be optionally fluorinated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3/$ carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

The compound of formula I is also provided with at least one co-feed organic compound. The compound preferably, though not exclusively, has a boiling point that is lower than the compound of Formula I, particularly 1230xa. Generally speaking, such compounds may include any halocarbon or haloolefin that exhibits the desired improvement in the reaction and/or improvement in the catalyst life. Non-limiting examples of such halocarbons and haloolefins include one or any combination of trichlorofluoropropene (1231), 2,3-dichloro-3,3-difluoropropene (1232xf), 1,2-dichloro-3,3,3-trifluoropropene (1223xd), 2-chloro-3,3,3-trifluoropropene (1233xf), 2-chloro-1,1,1,2-tetrachloropropane (244bb), 1,1,1,2,-pentafluoropropane (HFC-245cb), or one or more additional organic compounds that are typically generated during the fluorination reaction of 1230xa with HF. In one embodiment, the starting composition of Formula I (e.g. 1230xa), HF, and the at least one organic co-feed compounds are in the liquid phase; these are passed through a vaporizer and the resultant vapor phase materials being fed to the first vapor phase reactor.

The amount of co-feed compounds or an "effective amount," as used herein, relates to any amount that may be used to improve the conversion of a compound of formula I, particularly 1230xa, to 1233xf. In one aspect, the effective amount of co-feed organic compound may be any amount that measurably reduces the occurrence of oligomerization/polymerization of a compound of formula I during steam vaporization or during the fluorination reaction. Similarly, an effective amount may also, or independently, include any amount of the organic co-feed that results in a measurable reduction of catalyst deactivation, particularly deactivation caused by starting reagent oligomerization/polymerization. In one non-limiting embodiment, the percentage of co-feed organic(s) in total organic feed can be ranged from 0.1 to 99.9 wt %, from 1 to 50 wt %, from 3 to 30 wt %, or from 5 to 15 wt %, each based upon the total weight of organic reagents used. While not intending to be bound by theory, it is believed that co-feeding at least an organic compound with a lower boiling point than HCO-1230xa can facilitate the vaporization of HCO-1230xa and avoid/reduce the formation of HCO-1230xa oligomers, resulting in an improved catalyst life. In one embodiment, the co-feed compounds are provided as fresh feeds in effective amounts, i.e., they are not obtained from recycle streams derived from the multistep process. In another embodiment, the co-feed compounds are present in one or more recycle streams derived from the multistep process as described e.g. in U.S. Pat. No. 8,084,653 and US Published Patent Application 2009/0240090. In a practice of this embodiment, the invention is directed to a multistep process for preparing 2,3,3,3-tetrafluoropropene (1234yf) comprising: a.) contacting, in a first vapor phase reactor, in the presence of a vapor phase catalyst, a starting composition comprising at least one compound of formula I

$$CX_2=CCl-CH_2X \qquad (I)$$

wherein X is independently selected from F, Cl, Br, and I, provided that at least one X is not fluorine, with a fluorinating agent, to produce a first intermediate composition comprising 2-chloro-3,3,3trifluoropropene (1233xf), HCl and one or more organic co-feed compounds, said one or more organic co-feed compounds being other than the compound of formula I; b.) separating said HCl, said 2-chloro-3,3,3trifluoropropene (1233xf), and said one or more organic co-feed compounds from said first intermediate composition; c.) recycling an effective amount of said separated one or more organic co-feed compounds to said first vapor phase reactor; d.) contacting, in a liquid phase reactor, said separated 2-chloro-3,3,3trifluoropropene (1233xf) with a second fluorinating agent to produce a second intermediate composition comprising 2-chloro-1,1,1,2-tetrafluoropropane (244bb); and e.) dehydrochlorinating, in a second vapor phase reactor, at least a portion of said 2-chloro-1,1,1,2-tetrafluoropropane (244bb) to produce a reaction product comprising 2,3,3,3-tetrafluoropropene. In another practice of this embodiment, the recycling of said separated one or more organic co-feed compounds to said first vapor phase reactor in step c) provides said vapor phase catalyst with a longer catalyst life than in the absence of said recycling. In another practice of this embodiment, the vapor phase catalyst is selected from chromium oxide ($Cr_2O_3$), $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. In another practice of this embodiment, the effective amount of said separated one or more organic co-feed compounds recycled to said first vapor phase reactor in step c) is between about 1 to about 50 wt % based on the total weight of said starting composition in step a). In another practice of this embodiment, 244bb and/or 245cb are absent from the one or more organic co-feed compounds recycled to the first vapor phase reactor in step c), or alternatively, 244bb and/or 245cb are present in the recycle of step c) in insignificant amounts, e.g. the recycle is substantially free of 244bb and/or 245cb, which includes without limitation the presence of 244bb and/or 245cb in amounts that are not effective amounts. In another embodiment, the organic co-feeds can be a combination of fresh feed and recycle.

Optionally, the reaction may also include the use of one or more stabilizers. Generally speaking, such compounds may include an amine-based stabilizer. Non-limiting examples of such stabilizers suitable for use in the present reaction include those known for use in halogenation reactions, and in particular halogenation reactions involving alkanes, alkenes, and alkynes. In some embodiments, the stabilizer is selected from the group comprising p-tap(4-tert-Amylphenol), methoxy-hydroquinone, 4-methoxyphenol (HQMME), triethylamine, di-isopropyl amine, butylated hydroxy anisole (BHA), thymol and combinations thereof. In certain preferred embodiments, the stabilizer comprises an amine-based stabilizer. More preferably, the stabilizer comprises triethylamine, di-isopropyl amine or combinations thereof. The stabilizer is preferably present in an amount less than 300 ppm, more preferably in an amount less than 100 ppm, and most preferably, in an amount less than 10 ppm.

The HF, compound of formula I, and organic co-feed may be fed continuously to a vaporizer and the vaporized reactants to the catalyst bed. When the compound of formula I is 1230xa, the mol ratio of HF to 1230xa in step 1 of the reaction is 1:1 to 50:1 and, in certain embodiments, from about 10:1 to about 20:1. The reaction between HF and 1230xa is carried out at a temperature from about 150° C. to about 400° C. (in certain embodiments, about 180° C. to about 300° C.) and at a pressure of about 0 psig to about 200 psig (in certain embodiments from about 0 psig to about 100 psig). Contact time of the 1230xa with the catalyst may range from about 1 second to about 60 seconds, however, longer or shorter times can be used.

The fluorination reaction is preferably carried out to attain a conversion of about 50% or, preferably, about 90% or higher. Conversion is calculated by the number of moles of reactant (1230xa) consumed divided by number of moles of reactant (1230xa) fed to the reactor multiplied by 100. The selectivity for 1233xf attained is preferably about 60% or higher and more preferably about 80% or higher. Selectivity is calculated by number of moles of product (1233xf) formed divided by number of moles of reactant consumed.

This first step of the reaction may be conducted in any reactor suitable for a vapor phase fluorination reaction. In certain embodiments, the reactor is constructed from materials which are resistant to the corrosive effects of hydrogen fluoride and catalyst such as Hastalloy, Nickel, Incoloy, Inconel, Monel and fluoropolymer linings. The vessel is a fixed catalyst bed or fluidized bed. If desired, inert gases such as nitrogen or argon may be employed in the reactor during operation.

In general, the effluent from the fluorination reaction step, including any intermediate effluents that may be present in multi-stage reactor arrangements, may be processed to achieve desired degrees of separation and/or other processing. For example, in embodiments in which the reactor effluent includes 1233xf, the effluent will generally also include HCl and one or more of HF, dichlorodifluoropropenes (1232), 1,2-dichloro-3,3,3-trifluoropropene (1223xd), trichlorofluoropropene (1231) isomers, 2-chloro-1,1,1,2-tetrafluoropropane (244bb), and unreacted 1230xa. Some portion or substantially all of these components of the reaction product may be recovered from the reaction mixture via any separation or purification method known in the art such as neutralization and distillation. It is expected that unreacted 1230xa and HF could be recycled, completely or partially, to improve the overall yield of the desired 1233xf. 1232 and any 1231 formed may also be recycled.

Optionally, hydrogen chloride is then recovered from the result of the fluorination reaction. Recovering of hydrogen chloride is conducted by conventional distillation where it is removed from the distillate. Alternatively, HCl can be recovered or removed by using water or caustic scrubbers. When a water extractor is used, HCl is removed as an aqueous solution. When caustic scrubbers are used, HCl is just removed from system as a chloride salt in aqueous solution.

In the second step of the process for forming 2,3,3,3-tetrafluoroprop-1-ene, 1233xf is converted to 2-chloro-1,1,1,2-tetrafluoropropane (244bb). In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list include Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the 1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of 1234yf production, the 244bb is fed to a second vapor phase reactor (dehydrochlorination reactor) to be dehydrochlorinated to make the desired product 2,3,3,3-tetrafluoroprop-1-ene (1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

Preferred, but non-limiting, catalysts include activated carbon, stainless steel (e.g. SS 316), austenitic nickel-based alloys (e.g. Inconel 625), nickel, fluorinated 10% CsCl/MgO, and 10% $CsCl/MgF_2$. The reaction temperature is preferably about 300-550° C. and the reaction pressure may be between about 0-150 psig. The reactor effluent may be fed to a caustic scrubber or to a distillation column to remove the by-product of HCl to produce an acid-free organic product which, optionally, may undergo further purification using one or any combination of purification techniques that are known in the art.

The following are examples of the invention and are not to be construed as limiting.

EXAMPLES

Example 1

Fluorination of 1230xa Using 1230xa as Feed Stock 3 cc high surface area BASF chromium oxide was loaded into a ½ inch Hastelloy C 276 reactor. 6 inched Hastelloy B ⅛" distillation packing was packed on top of the catalyst as vaporizing zone. The catalyst was activated by HF first, then 1230xa was fed from top of the reactor at rate of 0.54 ml/hr together with 18 sccm HF and 3 sccm $N_2$ at 275° C. at atmospheric pressure. The stream from the reactor was analyzed by GC and GC-MS. The result of the test is shown in FIG. 1. The catalyst shows degradation over the time.

Example 2

Fluorination of 1230xa Using 1232xf-1230xa (1:1 Mol Ratio) Mixture as Feed Stock 3 cc high surface area BASF chromium oxide was loaded into a ½ inch Hastelloy C 276 reactor. 6 inched Hastelloy B ⅛" distillation packing was packed on top of the catalyst as vaporizing zone. The catalyst was activated by HF first, then 1232xf-1230xa mixture was fed from top of the reactor at rate of 0.53 ml/hr together with 18 sccm HF and 3 sccm $N_2$ at 275° C. at atmosphere pressure. The stream from the reactor was analyzed by GC and GC-MS. The result of the test is shown in FIG. 1. It shows improved catalyst life by using 1232xf-1230xa (1:1 mol ratio) mixture as feed stock.

Example 3

Fluorination of 1230xa Using 10 wt % 1233xf-90 wt % 1230xa Mixture as Feedstock

The 1230xa used in this example contained 5 ppm di-isopropyl amine. A mixture of 1.0 wt % 1233xf-90 wt % 1230xa was made as feedstock. 6.5 L of pre-fluorinated chromium oxide catalyst was loaded into a 4 inch Monel 400 reactor. The reactor was heated up to about 180° C. in nitrogen flow. Anhydrous HF feed was then started at a flow rate of 1.9 lb/h. After passing though a Mol Sieve 3A column at a flow rate of 1.1 lb/h, organic feed was combined with HF feed. The mixed HF and organic feed was introduced to a vaporizer for vaporization and then to the reactor for reaction. The reaction temperature (hot spot temperature) was increased to about 200° C. once the reaction was initiated. The reactor pressure was set at 70 psig. Samples were periodically taken from the product stream and were analyzed by GC and GC-MS during reaction. The results showed that 1230xa conversion was almost 100% and the average selectivities to 1233xf, 1232xf, 244bb were about 97.9%, 0.3%, and 1.5%, respectively, during the period of time of the reaction study that lasted for about 300 hours.

What is claimed is:

1. A process for preparing 2,3,3,3-tetrafluoroprop-1-ene comprising:
   a. vaporizing a fluorinating agent and a composition comprising a compound of formula I

CX$_2$=CCl—CH$_2$X            (I)

wherein X is independently selected from F, Cl, Br, and I, provided that at least one X is not fluorine and one or more organic co-feed compounds wherein said one or more organic co-feed compounds are other than the compound of Formula I,
   b. contacting the vaporized compound of Formula I and the vaporized fluorinating agent in the vapor phase in the presence of a fluorination catalyst to produce a first intermediate composition comprising 2-chloro-3,3,3-trifluoropropene;
   c. contacting said first intermediate composition with a second fluorinating agent to produce a second intermediate composition comprising 2-chloro-1,1,1,2-tetrafluoropropane; and
   d. dehydrochlorinating at least a portion of said 2-chloro-1,1,1,2-tetrafluoropropane to produce a reaction product comprising 2,3,3,3-tetrafluoroprop-1-ene.

2. The process of claim 1 wherein the organic co-feed compound has a boiling point that is lower than the compound of Formula I.

3. The process of claim 1, wherein the organic co-feed compound is a halocarbon or haloolefin.

4. The process of claim 1, wherein the organic co-feed compound is selected from the group consisting of trichlorofluoropropene (1231), dichlorodifluoropropene (1232), 1,2-dichloro-3,3,3-trifluoropropene (1223xd), 2-chloro-3,3,3-trifluoropropene (1233xf), 3,3,3,2-tetrafluoroprop-1ene (1234yf), 2-chloro-1,1,1,2-tetrafluoropropane, 1,1,1,2,2-pentafluoropropane (HFC-245cb), 1,1,1,2,3-pentafluoropropane (245eb), tetrachlorofluoropropane (241), trichlorodifluoropropane (242), dichlorotrifluoropropane (243) and combinations thereof.

5. The process of claim 1, wherein the effective amount of organic co-feed compound is between about 3 to about 30 wt %.

6. The process of claim 1, wherein the effective amount of organic co-feed compound is between about 1 to about 50 wt %.

7. The process of claim 1, wherein the effective amount of organic co-feed compound is between about 5 to about 15 wt %.

8. The process of claim 1, wherein at least one compound of formula I is a compound comprising at least one X is a chlorine.

9. The process of claim 1, wherein at least one compound of formula I is a compound where all Xs are chlorine.

10. The process of claim 1, wherein the at least one compound of formula I comprises 1,1,2,3-tetrachloropropene.

11. The process of claim 1, wherein the fluorination catalyst is a vapor phase catalyst selected from the group consisting of a chromium oxide, a chromium hydroxide, a chromium halide, a chromium oxyhalide, an aluminum oxide, an aluminum hydroxide, an aluminum halide, an aluminum oxyhalide, a cobalt oxide, a cobalt hydroxide, a cobalt halide, a cobalt oxyhalide, a manganese oxide, a manganese hydroxide, a manganese halide, a manganese oxyhalide, a nickel oxide, a nickel hydroxide, a nickel halide, a nickel oxyhalide, an iron oxide, an iron hydroxide, an iron halide, an iron oxyhalide, inorganic salts thereof, fluorinated derivatives thereof and combinations thereof.

12. The process of claim 11 wherein the fluorination catalyst comprises a chromium oxide.

13. A multistep process for preparing 2,3,3,3-tetrafluoropropene (1234yf) comprising:
   a.) vaporizing a starting composition comprising at least one compound of formula I

CX$_2$=CCl—CH$_2$X            (I)

wherein X is independently selected from F, Cl, Br, and I, provided that at least one X is not fluorine, and a fluorinating agent and one or more organic co-feed compounds, and contacting the vaporized compound of formula I with a fluorinating agent in the vapor phase in the presence of a fluorination catalyst, to produce a first intermediate composition comprising 2-chloro-3,3,3-trifluoropropene (1233xf), HCl and one or more organic co-feed compounds, said one or more organic co-feed compounds being other than the compound of formula I;
   b.) separating said HCl, said 2-chloro-3,3,3-trifluoropropene (1233xf), and said one or more organic co-feed compounds from said first intermediate composition;
   c.) recycling an effective amount of said separated one or more organic co-feed compounds to said first vapor phase reactor;
   d.) contacting, in a liquid phase reactor, said separated 2-chloro-3,3,3trifluoropropene (1233xf) with a second fluorinating agent to produce a second intermediate composition comprising 2-chloro-1,1,1,2-tetrafluoropropane (244bb); and
   e.) dehydrochlorinating, in a second vapor phase reactor, at least a portion of said 2-chloro-1,1,1,2-tetrafluoropropane (244bb) to produce a reaction product comprising 2,3,3,3-tetrafluoropropene.

14. The process of claim 13 wherein said fluorination catalyst is selected from Cr$_2$O$_3$, FeCl$_3$/C, Cr$_2$O$_3$/Al$_2$O$_3$, Cr$_2$O$_3$/AlF$_3$, Cr$_2$O$_3$/carbon, CoCl$_2$/Cr$_2$O$_3$/Al$_2$O$_3$, NiCl$_2$/Cr$_2$O$_3$/Al$_2$O$_3$, CoCl$_2$/AlF$_3$, NiCl$_2$/AlF$_3$ and mixtures thereof.

15. The process of claim 14 wherein said effective amount of said separated one or more organic co-feed compounds recycled to said first vapor phase reactor in step c) is between about 1 to about 50 wt % based on the total weight of said starting composition in step a).

16. The process of claim 13, wherein at least one compound of formula I is a compound wherein at least one X is a chlorine.

17. The process of claim 13, wherein at least one compound of formula I is a compound where all Xs are chlorine.

18. The process of claim 13, wherein the at least one compound of formula I comprises 1,1,2,3-tetrachloropropene.

19. The process of claim 13 wherein the catalyst comprises a chromium oxide.

20. The process of claim 13 wherein the one or more organic co-feed compounds has a boiling point that is lower than the compound of Formula I.

21. The process of claim 13 wherein the one or more organic co-feed compounds is selected from the group consisting of trichlorofluoropropene (1231), dichlorodifluoropropene (1232), 1,2-dichloro-3,3,3-trifluoropropene (1223xd), 2-chloro-3,3,3-trifluoropropene (1233xf), 3,3,3,2-tetrafluoroprop-1ene (1234yf), 2-chloro-1,1,1,2-tetrafluoropropane, 1,1,1,2,2-pentafluoropropane (HFC-245cb), 1,1,1,2,3-pentafluoropropane (245eb), tetrachlorofluoropropane (241), trichlorodifluoropropane (242), dichlorotrifluoropropane (243) and combinations thereof.

22. The process of claim 13 wherein the effective amount of the one or more co-feed compounds in (a) ranges from about 1 to about 50 wt %.

23. The process of claim 13 where the effective amount of the one or more co-feed organic compounds in (a) ranges from about 3 to about 30 wt %.

24. The process of claim 23 wherein the effective amount of the one or more organic co-feed compounds in (a) ranges from about 5 to about 15 wt %.

25. The process of claim 13 wherein the at least one compound of Formula I comprises 1,1,2,3-tetrachloropropene, the fluorination catalyst is chromium oxide, the fluorinating agent is anhydrous HF, and the one or more organic co-feed compounds is present in an amount ranging from 3 to 30 wt %.

26. The process of claim 1 wherein the at least one compound of Formula I comprises 1,1,2,3-tetrachloropropene, the fluorination catalyst is chromium oxide, the fluorinating agent is anhydrous HF, and the one or more organic co-feed compounds is present in an amount ranging from 3 to 30 wt %.

* * * * *